US007625711B2

(12) United States Patent
Nakagawara et al.

(10) Patent No.: US 7,625,711 B2
(45) Date of Patent: Dec. 1, 2009

(54) SCREENING METHOD FOR THE IDENTIFICATION OF A DRUG FOR THE DEVELOPMENT OF AN AGENT FOR PREVENTION AND/OR TREATMENT OF ALZHEIMER'S DISEASE

(75) Inventors: Akira Nakagawara, Chiba (JP); Toshinori Ozaki, Chiba (JP)

(73) Assignee: Hisamitsu Pharmaceutical Co., Inc., Chiba (JP)

( * ) Notice: Subject to any disclaimer, the term of this patent is extended or adjusted under 35 U.S.C. 154(b) by 27 days.

(21) Appl. No.: 10/570,346

(22) PCT Filed: Sep. 6, 2004

(86) PCT No.: PCT/JP2004/012955

§ 371 (c)(1),
(2), (4) Date: Jun. 6, 2006

(87) PCT Pub. No.: WO2005/023286

PCT Pub. Date: Mar. 17, 2005

(65) Prior Publication Data

US 2007/0218031 A1   Sep. 20, 2007

(30) Foreign Application Priority Data

Sep. 5, 2003   (JP)   ............................. 2003-314345

(51) Int. Cl.
*G01N 33/567*   (2006.01)
(52) U.S. Cl. ..................................................... 435/7.21
(58) Field of Classification Search ........................ None
See application file for complete search history.

(56) References Cited

U.S. PATENT DOCUMENTS

| 2003/0022171 A1 | 1/2003 | Sudhof et al. |
| 2003/0108929 A1 | 6/2003 | Sudhof et al. |
| 2003/0134323 A1 | 7/2003 | Sudhof et al. |

FOREIGN PATENT DOCUMENTS

WO   WO 02/79500 A1   10/2002

OTHER PUBLICATIONS

Kinoshita et al. Journal of Biological Chemistry, 277: 28530-28536, (2002).*
Xu et al. Proceedings of the National Academy of Sciences, USA, 96:7547-7552, (1999).*
Chen et al. Journal of Cell Biology 163(1): 27-33, (2003).*
Alves da Costa et al. The Journal of Neuroscience, 26(23):6377-6385, Jun. 2006.*
Vickers, Drugs Aging, 19(7):487-494, 2002.*
Donaldson et al. PNAS, 99(22):14053-14058, Oct. 2002.*
Pritchard JF, BMC Neuroscience, 9 Suppl 3:S1, Dec. 2008.*
T. Tomita at al., An amyloid hypothesis and Aβ42; Cell Technology, vol. 20, No. 11, pp. 1489-1494 (2001).

Xinwei Cao et al., "A transcriptively active complex of APP with Fe65 and histone acetyltransferase tip60," Science. vol. 293, pp. 115-120 (Jul. 2001).
Park et al., "Involvement of p53, JNK and NF-κB in CT-induced neuronal apoptosis," Society for Neuroscience Abstracts, vol. 27, No. 1, p. 1439 (2001).
Ayae Kinoshita at al., "The γ secretase-generated carboxyl-terminal domain of the amyloid precursor protein Induces apoptosis via tip60 in H4 cells," J. Biol. Chem., vol. 277, No. 32, pp. 28530-28536 (Aug. 2002).
Sionov at al., " The cellular response to p53: the decision between life and death," Oncogene, vol. 18, No. 45, pp. 6145-6157 (1999).
Yoichi Araki et al., "Coordinated metabolism of alcadein and amylold β-protein precursor regulates FE65-dependent gene transactivation," J. Biol. Chem., vol. 279, No. 23, pp. 24343-24354, (Jun. 2004).
"The β-Amyloid Precursor Protein APP is Tyrosine-Phosphorylated in Cells Expressing a Constitutively Active Form of the Abl Protoncogene", Zambrano, N. et al, Journal of Biological Chemistry, vol. 276, No. 23, ISSN: 0021-9258, Jun. 8, 2001, p19787-p19792, XP002530714.
"The c-Abl Tyrosine Kinase Phosphorylates the Fe65 Adaptor Protein to Stimulate Fe65/Amyloid Precursor Protein Nuclear Signaling", Perkinton, M. S. et al, Journal of Biological Chemistry, vol. 279, No. 21, ISSN: 0021-9258, Apr. 18, 2004, p22084- p22091, XP002530715.
P4-299, "Presenilin-Dependent Gamma-Secretase Cleavage of Alcadein and Amyloid Precursor Protein: Their Coordinative Metabolism and Cooperative Regulation on FE65-dependent Gene Transactivation", Araki, Y.et al, Neurobiology of Aging, vol. 25, ISSN: 0197-4580, Jul. 1, 2004, p5560, XP004626471.
"The Transcriptional Activity of the APP Intracellular Domain-Fe65 Complex is Inhibited by Activation of the NF-κB Pathway", Zhao, Q. et al, Biochemistry, vol. 42, No. 12, ISSN: 0006-2960, Aug. 3, 2003, p3627-p3634, XP002530716.
"The Intracellular Domain of the Low Density Lipoprotein Receptor-Related Protein Modulates Transactivation Mediated by Amyloid Precursor Protein and Fe65", Kinoshita, A. et al, Journal of Biological Chemistry, vol. 278, No. 42, ISSN: 0021-9258, Jul. 29, 2003, p41182-p41188, XP002480007.
"Activation of the Neuronal c-Abl Tyrosine Kinase by Amyloid-β-Peptide and Reactive Oxygen Species", Alvarez, A. R. et al, Neurobiology of Disease, vol. 17, No. 2, ISSN: 0969-9961, Nov., 2004, p326-p336, XP002530717.
European Search Report dated Jun. 18, 2009.

* cited by examiner

*Primary Examiner*—Olga N. Chernyshev
*Assistant Examiner*—Stacey MacFarlane
(74) *Attorney, Agent, or Firm*—Sughrue Mion, PLLC

(57) ABSTRACT

The present invention provides a novel drug/agent for the prevention and/or treatment of Alzheimer's disease based on a different Alzheimer's disease onset mechanism from the amyloid hypothesis, and a method of screening for it.

3 Claims, 18 Drawing Sheets

SCREENING METHOD FOR THE IDENTIFICATION OF A DRUG FOR THE DEVELOPMENT OF AN AGENT FOR PREVENTION AND/OR TREATMENT OF ALZHEIMER'S DISEASE

This Application is the National Phase of International Application No. PCT/JP2004/012955 filed Sep. 6, 2004, which designated the U.S. and was not published under PCT Article 21(2) in English, and this application claims, via the aforesaid International Application, the foreign priority benefit of and claims the priority from Japanese Application No. 2003-314345, filed Sep. 5, 2003, the complete disclosures of all the aforesaid applications, including any and all sequence listings, are incorporated herein by reference.

TECHNICAL FIELD

The present invention relates to an agent for the prevention and/or treatment of Alzheimer's disease, and to a method of screening for a drug for the prevention and/or treatment of Alzheimer's disease.

BACKGROUND ART

The overall picture of Alzheimer's disease which is a major cause of dementia in elderly people and the true cause of its onset have not yet been resolved, and no fundamental method has been proposed for its prevention and treatment. As to the mechanism for its onset, an "amyloid hypothesis" has been proposed. This is now widely accepted because of pathological findings of Alzheimer's disease patients, and genetic analyses of familial Alzheimer's disease (Non-Patent Document 1).

According to this hypothesis, an unusual accumulation of a group of proteins referred to as amyloid in the brain (cerebral cortex) is related to the onset and progression of Alzheimer's disease. To put it simply, an extracellular part of a single membrane-spanning protein referred to as βAPP (β-amyloid precursor protein) is cleaved by β-secretase (β-cleavage), the fragment on the C-terminal side is then cleaved by γ-secretase (γ-cleavage), and an N-terminal fragment (β40 or β42) and a C-terminal fragment (C60 or C58 (hereinafter collectively referred to also as AICD)) are produced. Among these fragments, the N-terminal fragment (β40 or β42) has high aggregability, and form amyloid, which accumulates as senile plaques outside the cell. The production, aggregation and accumulation of amyloid cause neuronal damage, which gives rise to neuronal death.

Non-Patent Document 1: Taisuke Tomita et al., Cell Technology, 2001, Vol. 20, No. 11, p. 1489-1494

DISCLOSURE OF THE INVENTION

Problem to be Solved by the Invention

Methods (drugs) for the prevention and/or treatment of Alzheimer's disease have been developed based on the "amyloid hypothesis." Examples of these drugs are inhibitors of β-secretase and γ-secretase, and anti-amyloid antibodies. However, it has been pointed out that Alzheimer's disease is a multifactoral disease, and that a drug design based only on the amyloid hypothesis is not sufficient to provide a method (drug) for the prevention and/or treatment of Alzheimer's disease.

It is therefore an object of the present invention to provide a novel drug/agent for the prevention and/or treatment of Alzheimer's disease based on a different Alzheimer's disease onset mechanism from the amyloid hypothesis, and a method of screening for it.

Means for Solving the Problem

In order to achieve this object, the present invention provides a screening method wherein a candidate drug which inhibits the interaction between AICD and p53 in neurons is selected as a drug for the prevention and/or treatment of Alzheimer's disease. Using this screening method, a novel drug/agent for the prevention and/or treatment of Alzheimer's disease based on a different Alzheimer's disease onset mechanism from the amyloid hypothesis can be obtained.

This screening method preferably comprises:

a step of culturing neurons expressing AICD and p53 in which an AICD/p53 complex is formed, together with a candidate drug;

a step of obtaining a first immune complex which is a complex of AICD or p53 with a first antibody selected from an anti-AICD antibody and an anti-p53 antibody, and a second immune complex which is a complex of the AICD/p53 complex with the first antibody, by bringing a cell lysate prepared from the cultured neurons in contact with the first antibody;

a step of bringing the first and second immune complexes in contact with a second antibody which is selected from an anti-AICD antibody and an anti-p53 antibody, and which is different from the first antibody; and a step of detecting the presence of a third immune complex which is a complex of the second immune complex with the second antibody.

A drug for the prevention and/or treatment of Alzheimer's disease which can be obtained by such a screening method can be a medicinal ingredient of an agent for the prevention and/or treatment of Alzheimer's disease.

As such an agent, there is provided an agent for the prevention and/or treatment of Alzheimer's disease containing c-Abl and/or $p19^{ARF}$ as (an) active ingredient(s).

p53 is a transcription factor present in the nucleus responsible for cell cycle regulation and DNA repair, and leads to cell differentiation, cellular senescence, angiogenesis and cell death (apoptosis). As for AICD, its behavior in the cell and its relationship to Alzheimer's disease were not well understood, but recently it was reported that AICD localizes to the nucleus to participate in transcription activation (Xinwei Cao et al., Science, 293, 115-120 (2001)).

The present inventors considered, as a possible molecular biological mechanism for the onset of Alzheimer's disease, that AICD localizes to the nucleus where it interacts with p53 in some way, and as a result, neurons suffer apoptosis more easily, which gives rise to the onset of Alzheimer's disease. FIG. 1 is a schematic diagram describing the amyloid hypothesis, and the involvement of the interaction between AICD and p53 in the onset of Alzheimer's disease.

The present inventors found that stabilization of p53 by the interaction between AICD and p53 increases the transcription factor activity of p53, and unique activities of p53 such as cell proliferation-suppressing activity and cell death-inducing activity, and thereby induces neuronal death. Based on this finding, they reasoned that a substance which could inhibit the interaction between AICD and p53 would be useful as a drug for the prevention and/or treatment of Alzheimer's disease.

c-Abl and $p19^{ARF}$ are proteins which antagonistically regulate the binding of Mdm2 to p53 (R. V Sionov et al., Oncogene, 18, 6145-6157 (1999)), and might therefore inhibit the interaction between AICD and p53.

The present invention also provides a screening method wherein a candidate drug which inhibits the interaction between AICD and Fe65 in neurons is selected as a drug for the prevention and/or treatment of Alzheimer's disease. Also using this screening method, a novel drug/agent for the prevention and/or treatment of Alzheimer's disease based on a different Alzheimer's disease onset mechanism from the amyloid hypothesis can be obtained.

This screening method preferably comprises:

a step of culturing neurons expressing AICD and Fe65 in which an AICD/Fe65 complex is formed, together with a candidate drug;

a step of obtaining a first immune complex which is a complex of AICD or Fe65 with a first antibody selected from an anti-AICD antibody and an anti-Fe65 antibody, and a second immune complex which is a complex of the AICD/Fe65 complex with the first antibody, by bringing a cell lysate prepared from the cultured neurons in contact with the first antibody;

a step of bringing the first and second immune complexes in contact with a second antibody which is selected from an anti-AICD antibody and an anti-Fe65 antibody, and which is different from the first antibody; and a step of detecting the presence of a third immune complex which is a complex of the second immune complex with the second antibody.

A drug for the prevention and/or treatment of Alzheimer's disease which can be obtained by such a screening method can be a medicinal ingredient of an agent for the prevention and/or treatment of Alzheimer's disease.

As such an agent, there is provided an agent for the prevention and/or treatment of Alzheimer's disease containing AlcICD as an active ingredient. There is also provided an agent for the prevention and/or treatment of Alzheimer's disease containing a peptide which comprises the amino acid sequence set forth in SEQ ID NO: 1 or 2 of the Sequence Listing as an active ingredient.

It is known that the nuclear receptor protein Fe65 forms a complex with AICD, and that it activates transcription mediated by a fusion protein of Gal4 and histone acetyl transferase Tip60 (Xinwei Cao et al., Science, 293, and 115-120 (2001)). Based on this knowledge, the present inventors reasoned that Fe65 is a substance which promotes the nuclear localization of AICD by interacting with AICD, and that a substance which could inhibit the interaction between AICD and Fe65 would indirectly inhibit the interaction between AICD and p53, and therefore suppress the onset of Alzheimer's disease.

AlcICD is a substance which inhibits the interaction between AICD and Fe65 (Araki, Y et al., J. Biol. Chem., 279, 24343-24354 (2004)). It is known that the binding site of AICD in Fe65 is the PTB2 domain, and that the amino acid sequence of the binding site of Fe65 in AICD is the NPTY sequence (Xinwei Cao et al., Science, 293, 115-120 (2001)). SEQ ID NO: 1 of the Sequence Listing is an arrangement showing the amino acid sequence of the PTB2 domain in Fe65. SEQ ID NO: 2 of the Sequence Listing is an arrangement showing the NPTY sequence. It is thought that a peptide which comprises the amino acid sequence of SEQ ID NO: 1 or 2 of the Sequence Listing inhibits the interaction between AICD and Fe65.

The present invention also provides a screening method wherein a candidate drug which inhibits the interaction between AICD and Tip60 in neurons is selected as a drug for the prevention and/or treatment of Alzheimer's disease. Also using this screening method, a novel drug/agent for the prevention and/or treatment of Alzheimer's disease based on a different Alzheimer's disease onset mechanism from the amyloid hypothesis can be obtained.

This screening method preferably comprises:

a step of culturing neurons expressing AICD and Tip60 in which an AICD/Tip60 complex is formed, together with a candidate drug;

a step of obtaining a first immune complex which is a complex of AICD or Tip60 with a first antibody selected from an anti-AICD antibody and an anti-Tip60 antibody, and a second immune complex which is a complex of the AICD/Tip60 complex with the first antibody, by bringing a cell lysate prepared from the cultured neurons in contact with the first antibody;

a step of bringing the first and second immune complexes in contact with a second antibody which is selected from an anti-AICD antibody and an anti-Tip60 antibody, and which is different from the first antibody; and a step of detecting the presence of a third immune complex which is a complex of the second immune complex with the second antibody.

A drug for the prevention and/or treatment of Alzheimer's disease which can be obtained by such a screening method can be a medicinal ingredient of an agent for the prevention and/or treatment of Alzheimer's disease.

It is known that histone acetyl transferase Tip60 forms a complex with AICD and causes cell death (apoptosis) of glioma cells (Ayae Kinoshita et al., J. Biol. Chem., 277, 28530-28536 (2002)). Based on this knowledge, the present inventors reasoned that Tip60 is a substance which promotes the interaction between AICD and p53, and that a substance which could inhibit the interaction between AICD and Tip60 would be useful as a drug for the prevention and/or treatment of Alzheimer's disease.

Effects of the Invention

According to the present invention, it is possible to provide a novel drug/agent for the prevention and/or treatment of Alzheimer's disease based on a different Alzheimer's disease onset mechanism from the amyloid hypothesis, and a method of screening for it.

BEST MODES FOR CARRYING OUT THE INVENTION

Preferred embodiments of the present invention will now be described.

(Interaction Between AICD and p53)

The interaction of βAPP or AICD with p53 can be examined by performing assays regarding activities of p53 such as transcription factor activity and cell death-inducing activity (apoptosis activity) in the presence of βAPP and/or AICD.

Effect of βAPP on the transcription factor activity of p53:

It is known that if the p53 gene is introduced into a U2OS cell expressing p53, the activities of promoters which reacts to p53 (the p21, MDM2 and Bax promoters) will increase. Therefore, it is examined whether or not the activities of these promoters increase when the βAPP-encoding gene is introduced instead of p53. The luciferase assay (luciferase reporter assay), which is a standard technique for analyzing the function of a transcription factor, is used for the test.

Specifically, βAPP expression vector, and reporter vector containing a promoter which reacts to p53 (the p21, MDM2 or Bax promoter) are introduced into U2OS cells expressing wild-type p53. After 48 hours, the cells are collected and the luciferase activity is measured. The luciferase activity measurement results thus obtained for the promoters are shown in FIGS. 2-4.

Figure 1:
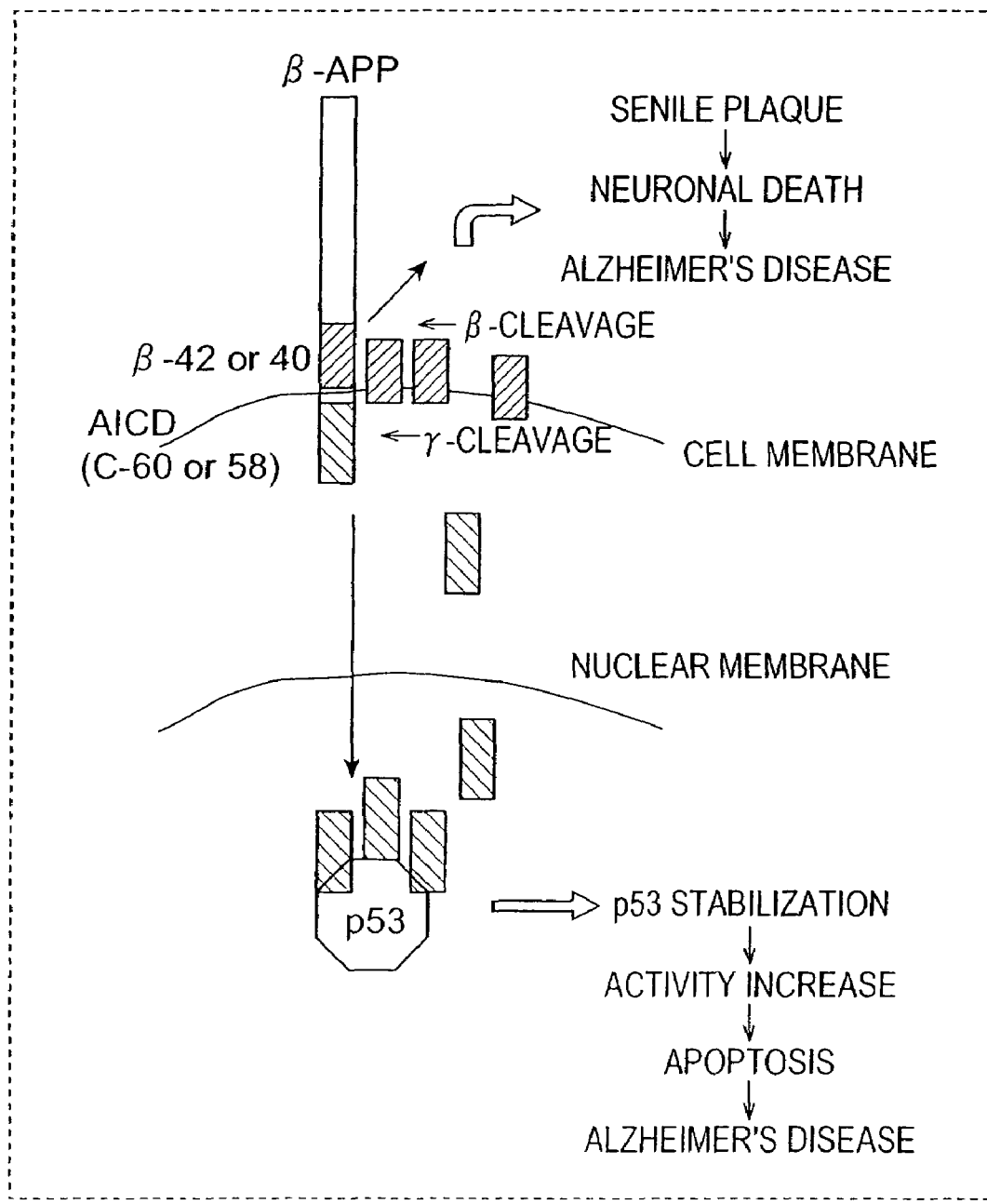
FIG. 1 is a schematic diagram describing the amyloid hypothesis, and the involvement of the interaction between AICD and p53 in the onset of Alzheimer's disease.
Figure 2:
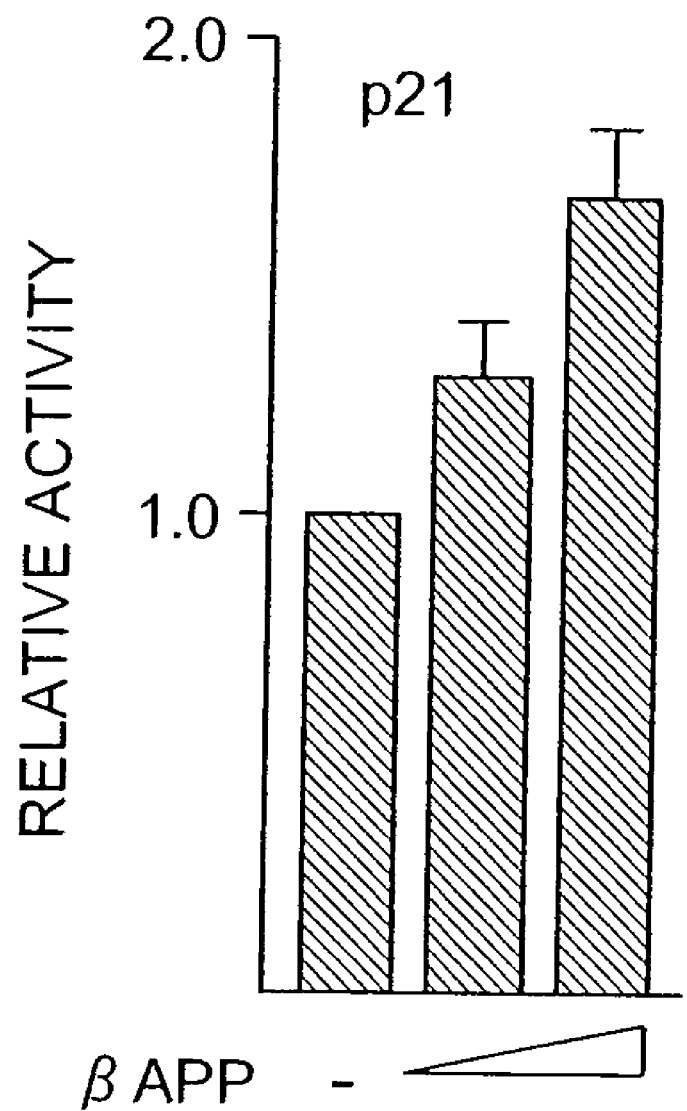
FIG. 2 is a graph showing the activity of the p21 promoter when βAPP is forcibly expressed in p53-expressing cells.

FIG. 2 is a graph showing the activity of the p21 promoter when βAPP is forcibly expressed in p53-expressing cells. FIG. 3 is a graph showing the activity of the MDM2 promoter when βAPP is forcibly expressed in p53-expressing cells. FIG. 4 is a graph showing the activity of the Bax promoter when βAPP is forcibly expressed in p53-expressing cells.

Figure 3:
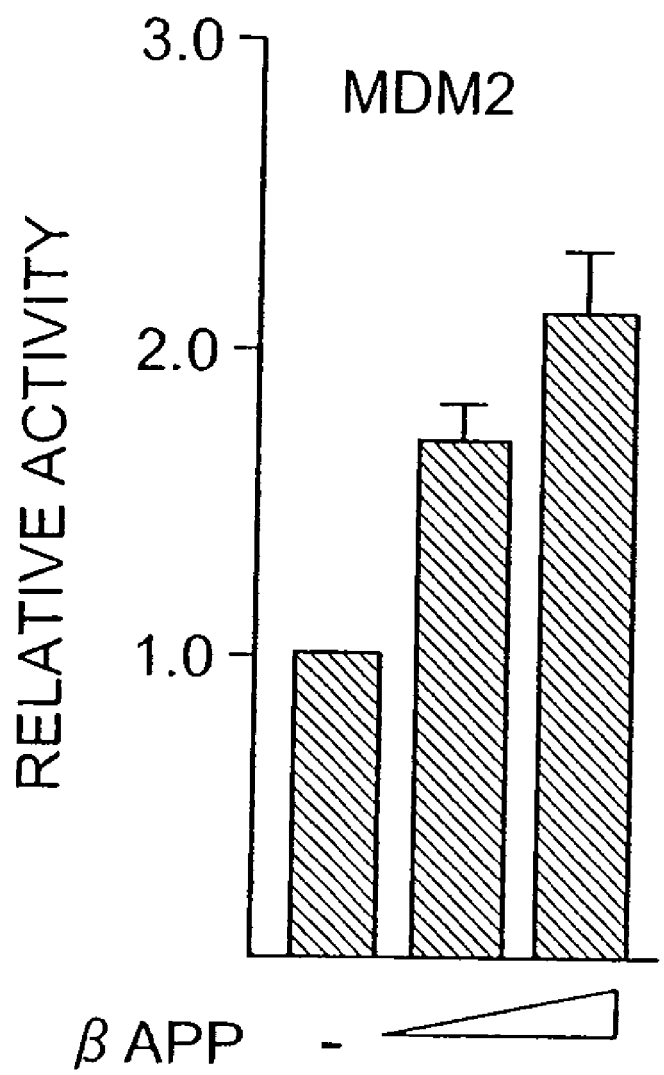
FIG. 3 is a graph showing the activity of the MDM2 promoter when βAPP is forcibly expressed in p53-expressing cells.
Figure 4:
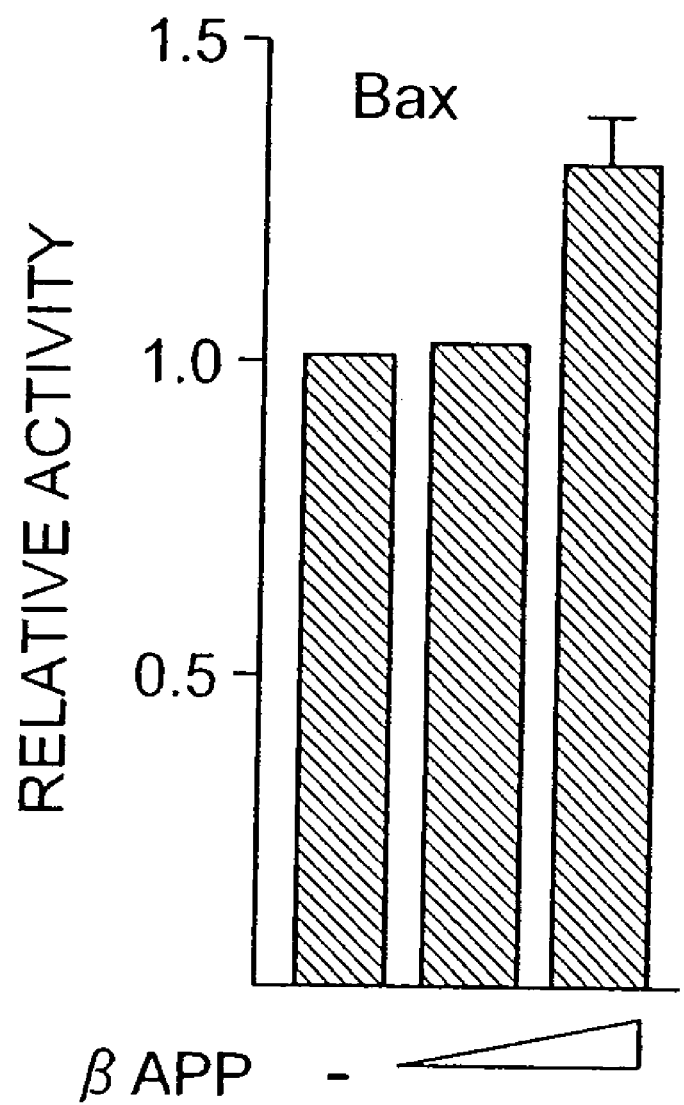
FIG. 4 is a graph showing the activity of the Bax promoter when βAPP is forcibly expressed in p53-expressing cells.

From FIGS. 2-4, it can be seen that for any of the p21, MDM2 and Bax-derived promoters, the activity markedly increases due to the forced expression of βAPP. It is thought that βAPP produces C60 or C58 using an endogenous secretase. Moreover, U2OS cells express wild-type p53. Therefore, the activation of p53 by C60 or C58 is suggested.

Next, it is examined whether or not the activity of p53 increases by using p53 and βAPP together. The luciferase assay is used for the test as in the case described above.

Specifically, βAPP expression vector, p53 expression vector, and reporter vector containing a promoter which reacts to p53 (the p21, MDM2 or Bax promoter) are introduced into U2OS cells expressing wild-type p53. After 48 hours, the cells are collected and the luciferase activity is measured. The luciferase activity measurement results thus obtained for the promoters are shown in FIGS. 5-7.

Figure 5:
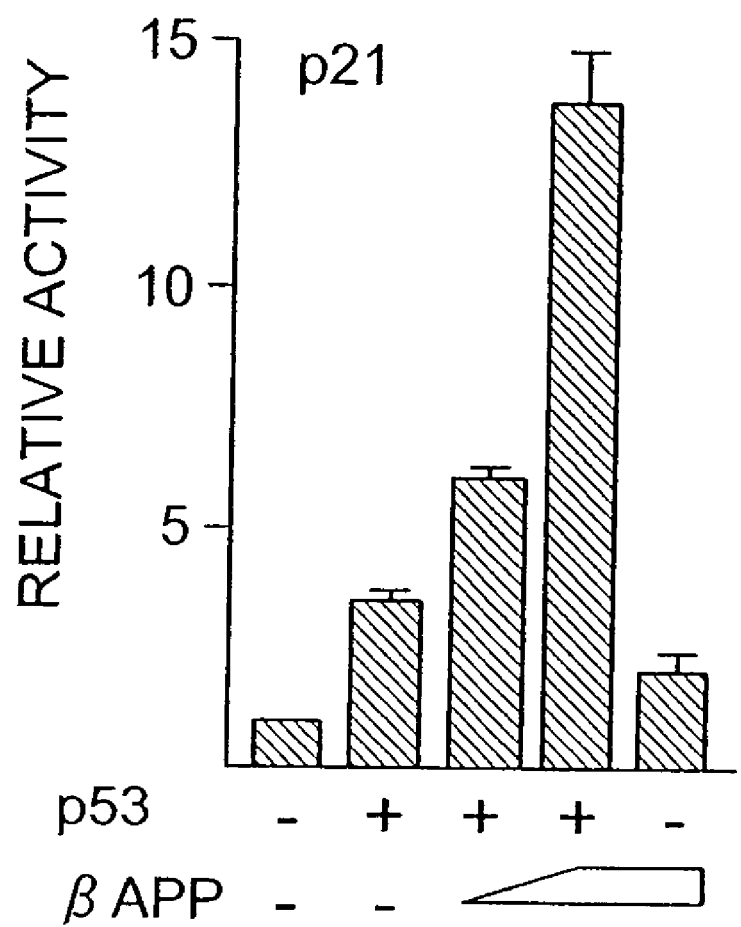
FIG. 5 is a graph showing the activity of the p21 promoter when βAPP and p53 are forcibly expressed in p53-expressing cells.

FIG. 5 is a graph showing the activity of the p21 promoter when βAPP and p53 are forcibly expressed in p53-expressing cells. FIG. 6 is a graph showing the activity of the MDM2 promoter when βAPP and p53 are forcibly expressed in p53-expressing cells. FIG. 7 is a graph showing the activity of the Bax promoter when βAPP and p53 are forcibly expressed in p53-expressing cells.

Figure 6:
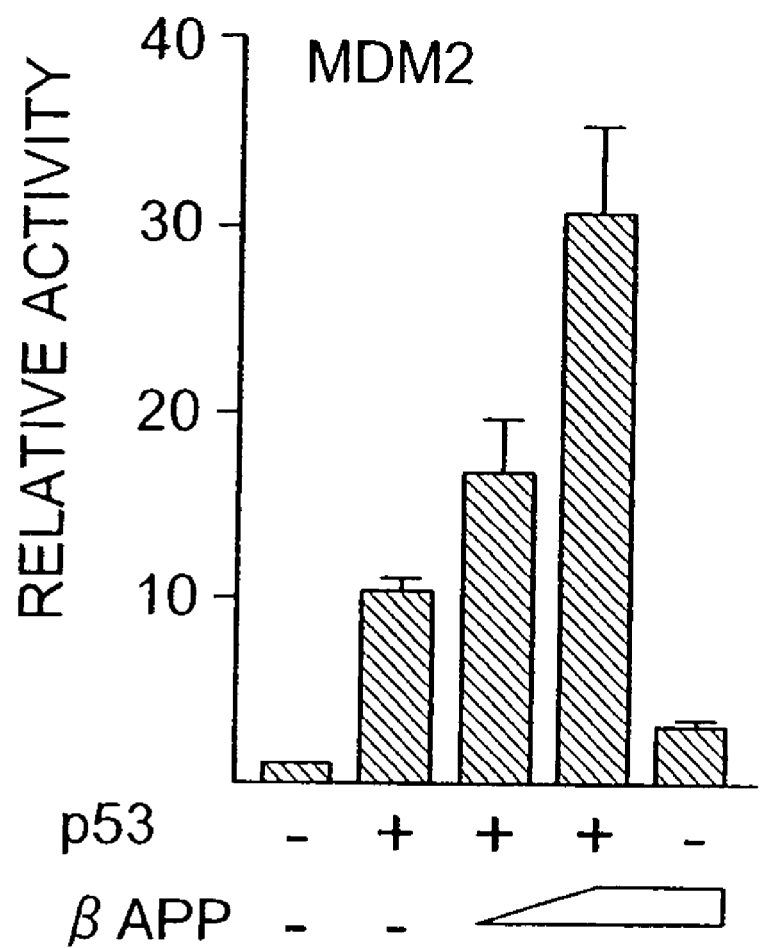
FIG. 6 is a graph showing the activity of the MDM2 promoter when βAPP and p53 are forcibly expressed in p53-expressing cells.
Figure 7:
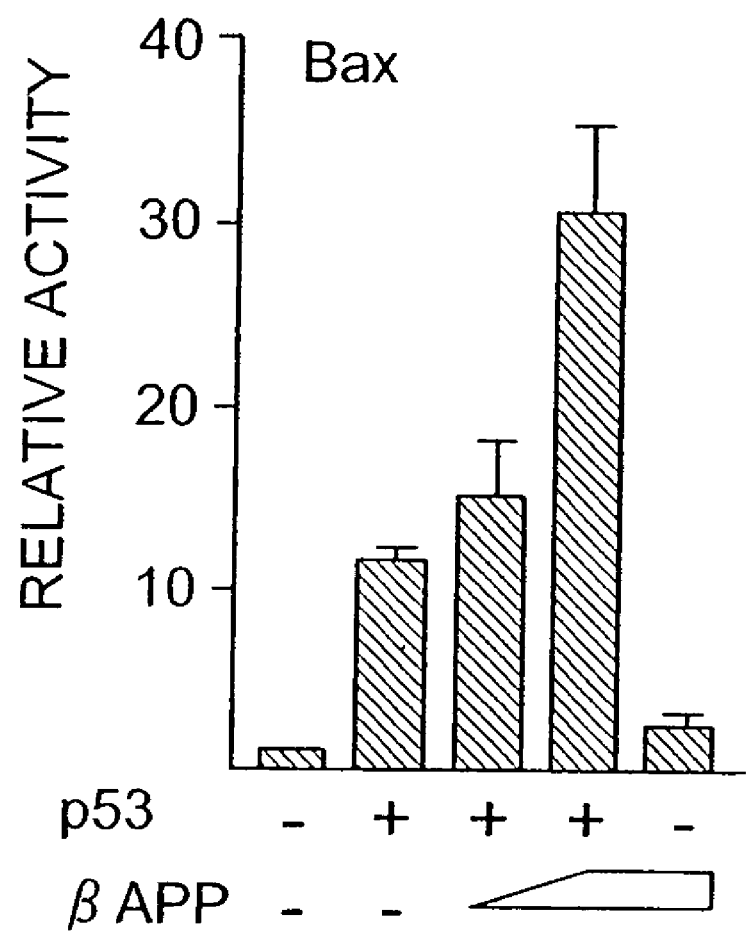
FIG. 7 is a graph showing the activity of the Bax promoter when βAPP and p53 are forcibly expressed in p53-expressing cells.

From FIGS. 5-7, it can be seen that for any of the p21, MDM2 and Bax-derived promoters, the activity markedly increases when βAPP and p53 are forcibly expressed, compared with the case where βAPP is forcibly expressed alone. Therefore, the activation of p53 by C60 or C58 is suggested as in the test described above.

As a negative control, the same test is repeated using cells which do not express p53.

βAPP expression vector, and reporter vector containing a promoter which reacts to p53 (the p21, MDM2 or Bax promoter) are introduced into H1299 cells lacking wild-type p53. After 48 hours, the cells are collected and the luciferase activity is measured. The luciferase activity measurement results thus obtained for the promoters are shown in FIGS. 8-10.

Figure 8:
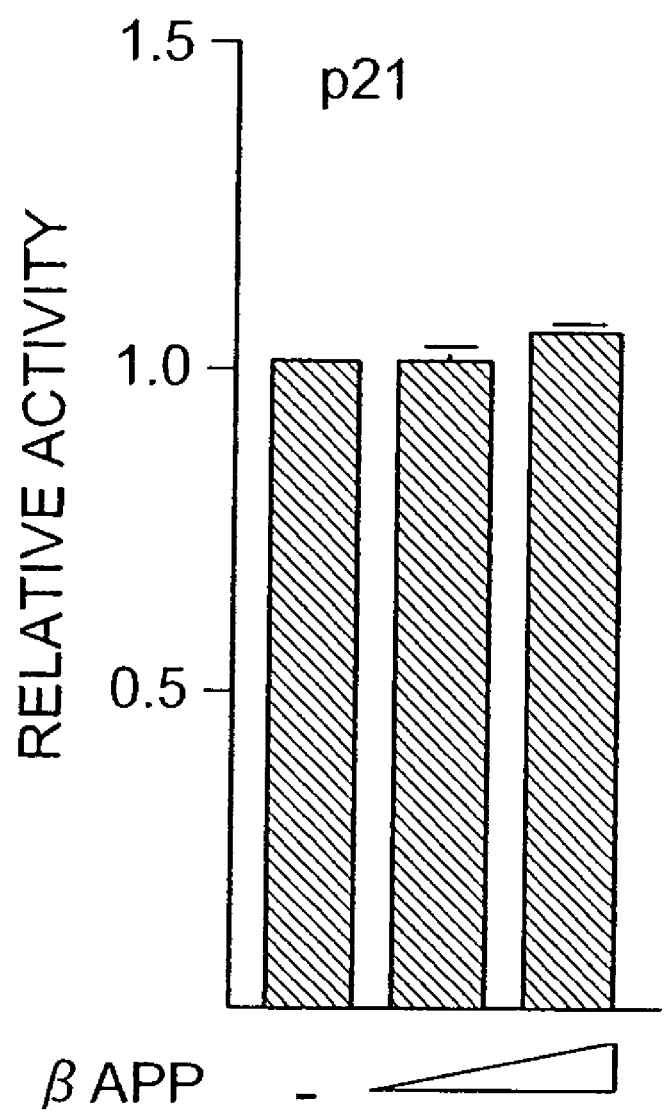
FIG. 8 is a graph showing the activity of the p21 promoter when βAPP is forcibly expressed in non-p53-expressing cells.

FIG. 8 is a graph showing the activity of the p21 promoter when βAPP is forcibly expressed in non-p53-expressing cells. FIG. 9 is a graph showing the activity of the MDM2 promoter when βAPP is forcibly expressed in non-p53-expressing cells. FIG. 10 is a graph showing the activity of the Bax promoter when βAPP is forcibly expressed in non-p53-expressing cells.

Figure 9:
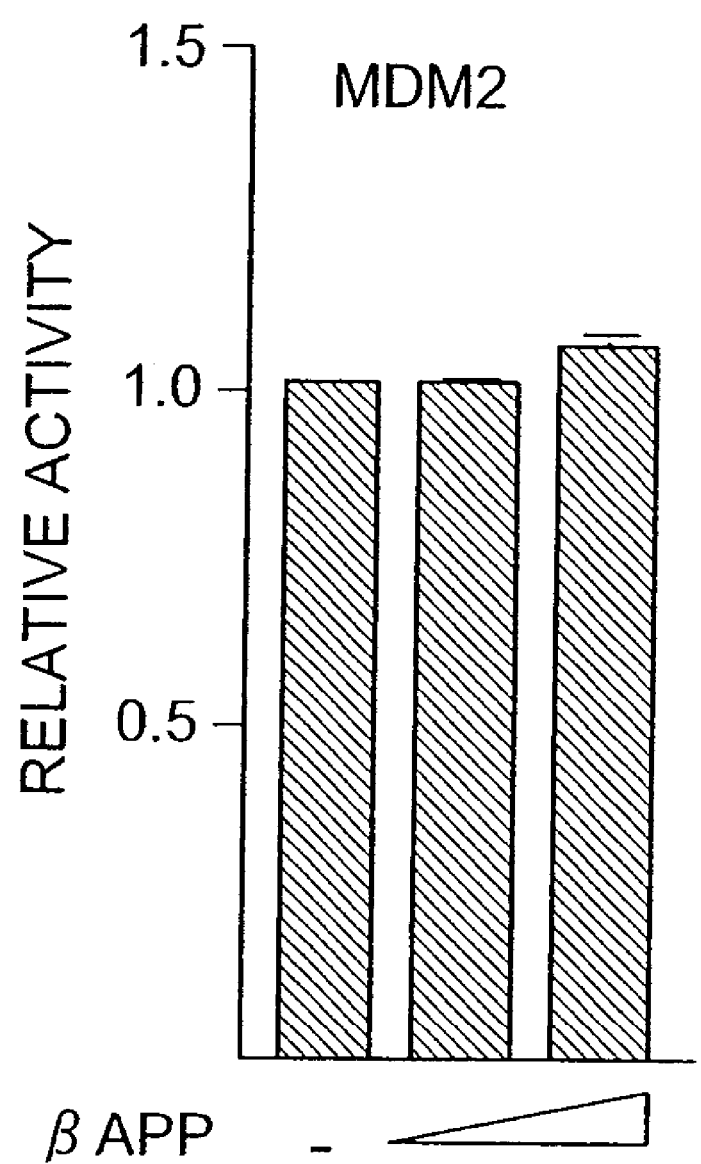
FIG. 9 is a graph showing the activity of the MDM2 promoter when βAPP is forcibly expressed in non-p53-expressing cells.
Figure 10:
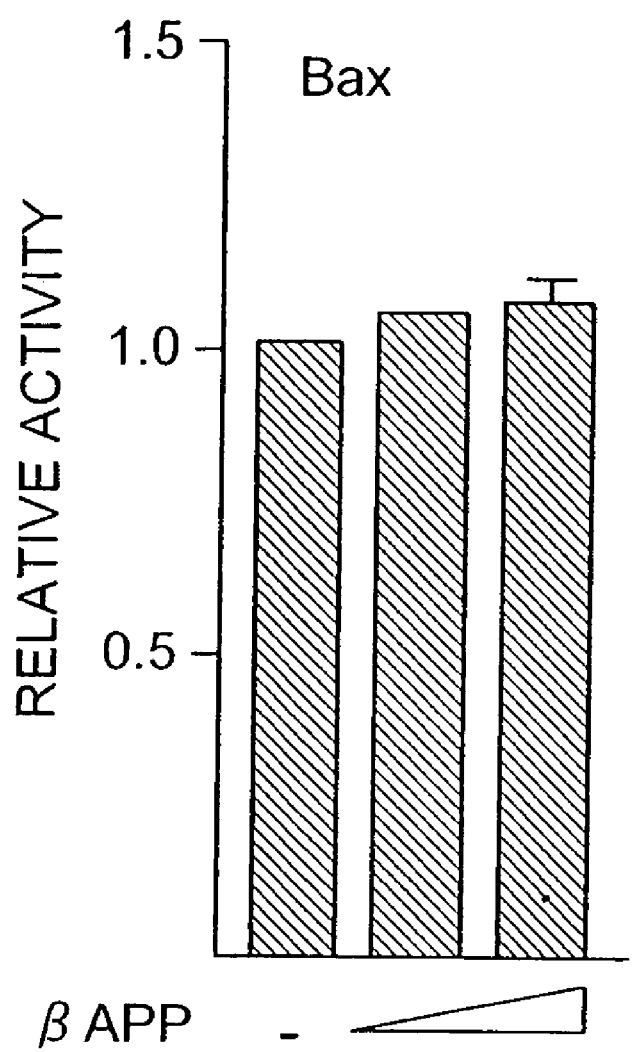
FIG. 10 is a graph showing the activity of the Bax promoter when βAPP is forcibly expressed in non-p53-expressing cells.

From FIGS. 8-10, it can be seen that for any of the p21, MDM2 and Bax-derived promoters, the activity does not increase even due to the forced expression of βAPP. Since H1299 cells lack wild-type p53, it is suggested that the activation of the p21, MDM2 and Bax promoters by βAPP observed in the U2OS cells mentioned above is caused by the activation of p53 by βAPP.

Figure 11:
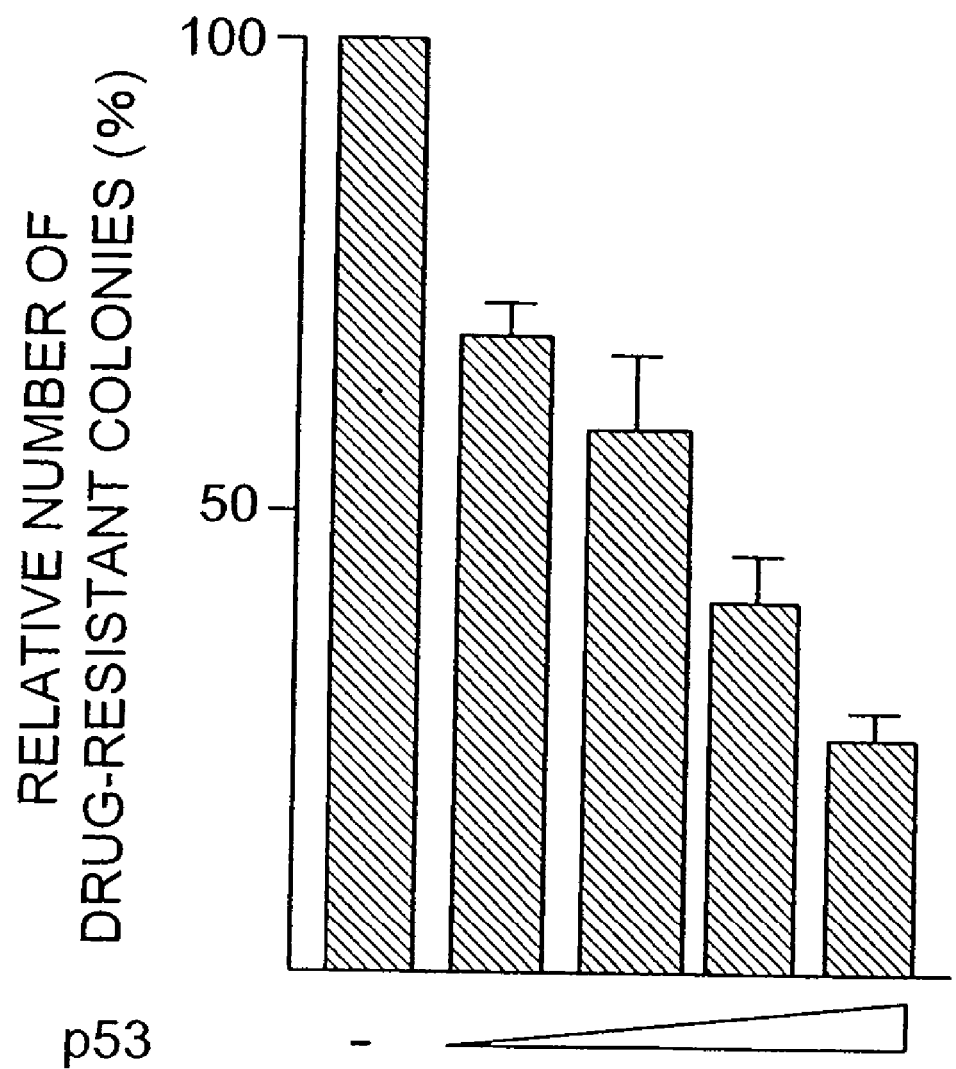
FIG. 11 is a graph showing the drug-resistant colony count when p53 is forcibly expressed in p53-expressing cells.

Cell proliferation-suppressing activity and cell death-inducing activity of p53:

It is examined whether or not p53 exhibits its inherent cell proliferation-suppressing activity and cell death-inducing activity in the U2OS cells used in the test described above.

p53 expression vector is introduced into U2OS cells expressing wild-type p53, and then the cells are cultured in the presence of G418. After 2 weeks, the G418-resistant colony count is measured. The obtained result is shown in FIG. 11. FIG. 11 is a graph showing the drug-resistant colony count when p53 is forcibly expressed in p53-expressing cells.

From FIG. 11, it can be seen that the G418-resistant colony count markedly decreases due to the forced expression of p53. Therefore, it can be seen that in U2OS cells, p53-dependent suppression of cell proliferation or p53-dependent cell death does occur.

Figure 12:
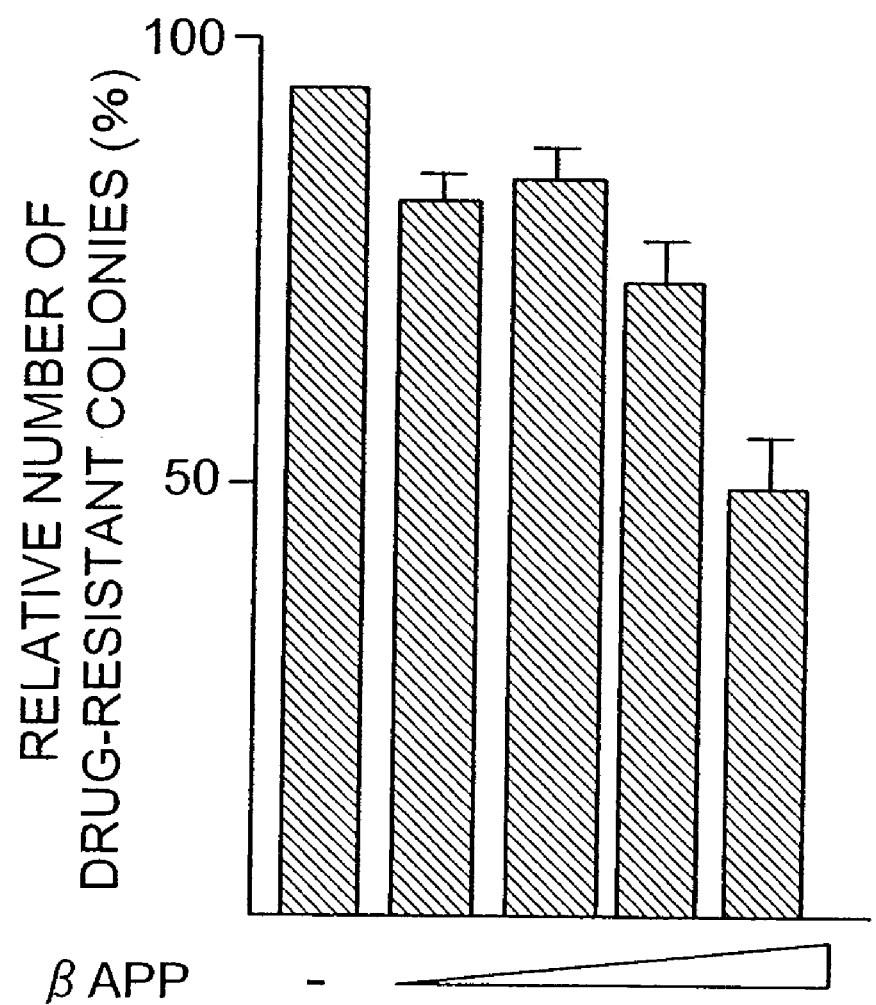
FIG. 12 is a graph showing the drug-resistant colony count when βAPP is forcibly expressed in p53-expressing cells.

Effect of βAPP on the cell proliferation-suppressing activity and cell death-inducing activity of p53:

Next, it is examined whether or not the cell proliferation-suppressing activity and cell death-inducing activity of endogenous p53 change due to the introduction of βAPP. The colony formation assay is used for the test as in the case described above.

βAPP expression vector is introduced into U2OS cells expressing wild-type p53, and then the cells are cultured in the presence of G418. After 2 weeks, the G418-resistant colony count is measured. The obtained result is shown in FIG. 12. FIG. 12 is a graph showing the drug-resistant colony count when βAPP is forcibly expressed in p53-expressing cells.

From FIG. 12, it can be seen that the G418-resistant colony count decreases due to the forced expression of βAPP. Therefore, it can be seen that in U2OS cells, βAPP-dependent suppression of cell proliferation or βAPP-dependent cell death does occur.

Figure 13:
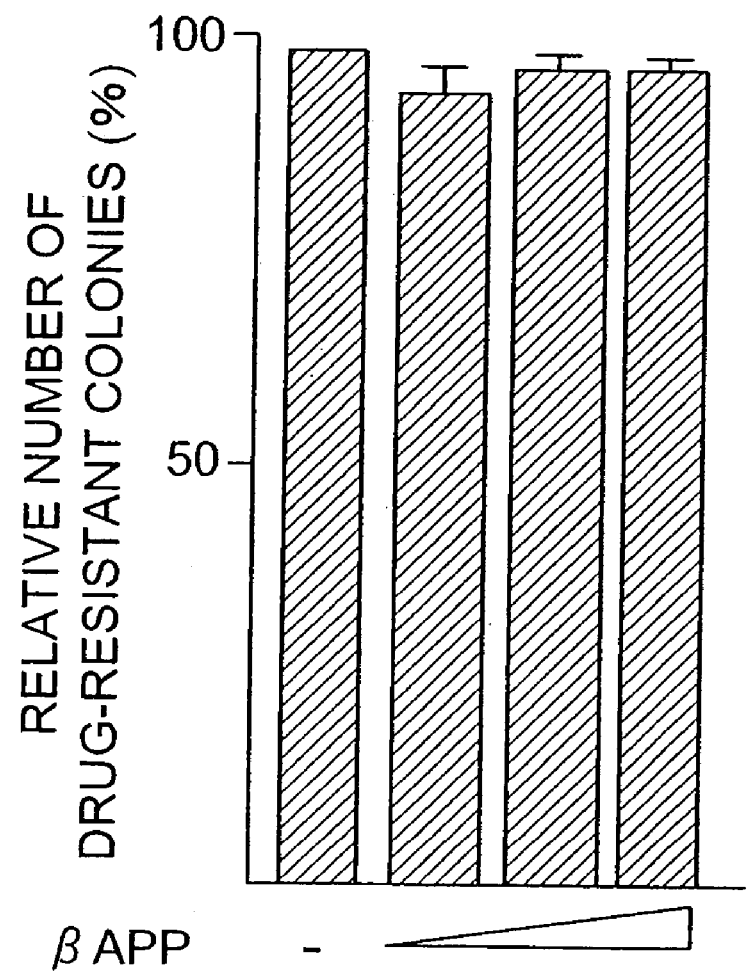
FIG. 13 is a graph showing the drug-resistant colony count when βAPP is forcibly expressed in non-p53-expressing cells.

As a negative control, the same test is repeated in H1299 cells which do not express wild-type p53. Specifically, βAPP expression vector is introduced into H1299 cells lacking wild-type p53, and then the cells are cultured in the presence of G418. After 2 weeks, the G418-resistant colony count is measured. The obtained result is shown in FIG. 13. FIG. 13 is a graph showing the drug-resistant colony count when βAPP is forcibly expressed in non-p53-expressing cells.

From FIG. 13, it can be seen that the drug-resistant colony count does not decrease even due to the forced expression of βAPP. It is therefore thought that the presence of wild-type p53 is required for βAPP-dependent suppression of cell proliferation or βAPP-dependent induction of cell death, which are observed in the test described above.

Induction of cell death by cisplatin:

It is known that if tumor cells are treated with cisplatin, which is a DNA-inhibiting drug, dose-dependent cell death occurs. It is also known that p53 is involved in this. The relationship of βAPP to the induction of cell death by p53 is investigated using cisplatin, which is known to induce endogenous p53. For this purpose, the induction of cell death by cisplatin is examined.

Figure 14:
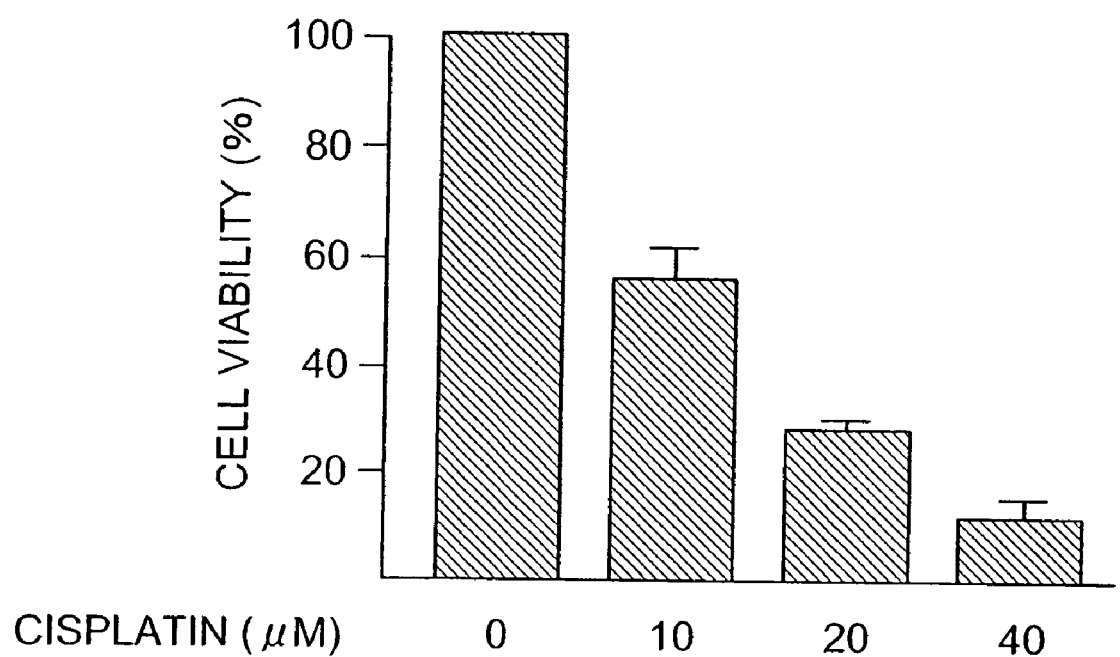
FIG. 14 is a graph showing the relationship between the amount of cisplatin and the cell viability of SH-SY5Y cells.

SH-SY5Y cells, which are a neuroblastoma cell line, are used as tumor cells. SH-SY5Y cells are treated with cisplatin, and then the cell viability is measured by the MTT method. The obtained result is shown in FIG. 14. FIG. 14 is a graph showing the relationship between the amount of cisplatin and the cell viability of SH-SY5Y cells.

From FIG. 14, it can be seen that the number of SH-SY5Y cells decreases depending on the dosage of cisplatin. It can be seen that the death of SH-SY5Y cells is induced by cisplatin.

Figure 15:
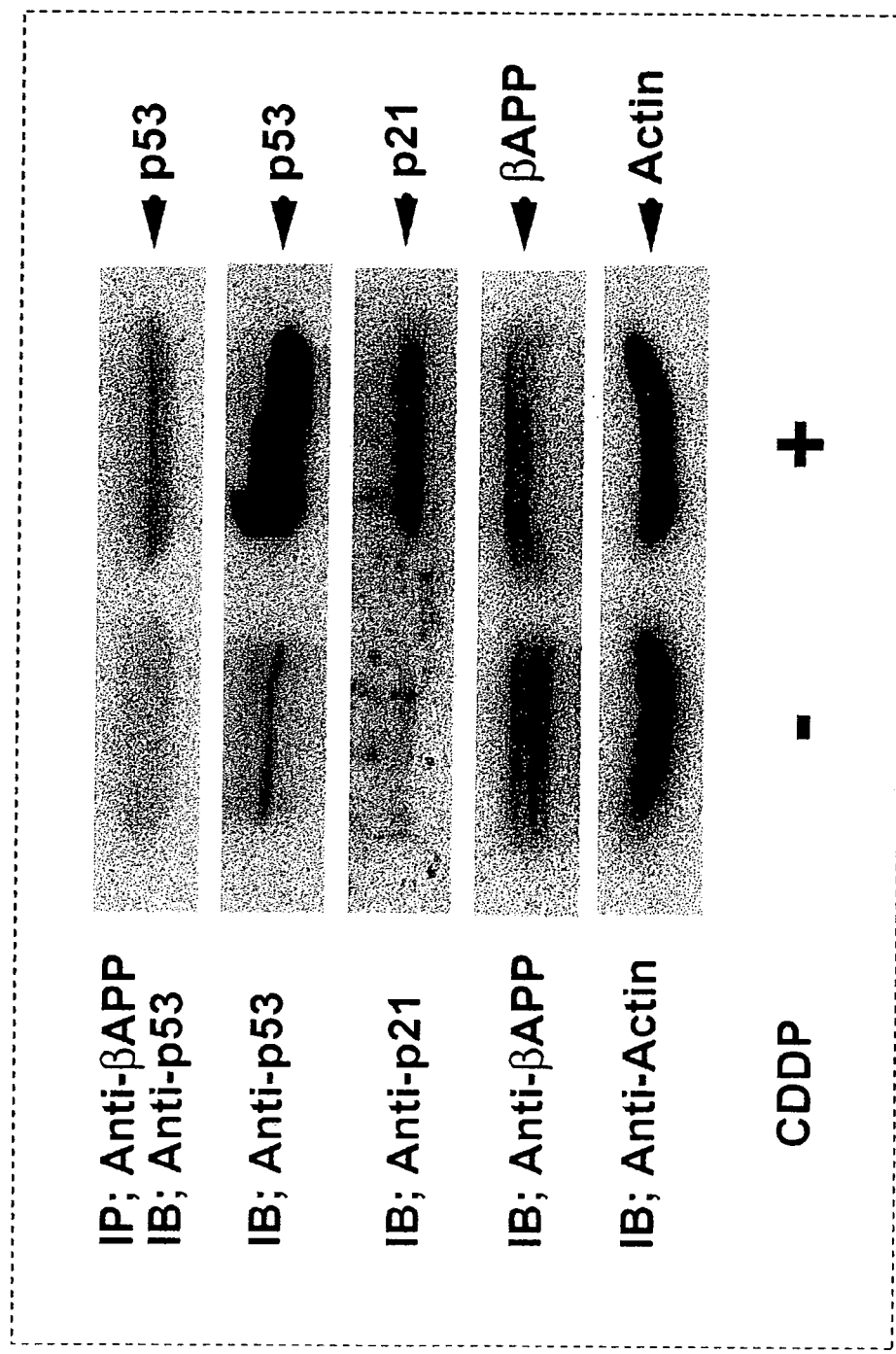
FIG. 15 is diagrams showing the result of immunoblotting analysis of products obtained by cisplatin treatment of SH-SY5Y cells.

Next, products obtained by cisplatin treatment of SH-SY5Y cells are analyzed by immunoblotting and immunoprecipitation. Specifically, SH-SY5Y cells are treated with cisplatin, and then the expression levels of p53, p21, βAPP and actin are analyzed by immunoblotting. Moreover, an interaction between a βAPP-derived product and p53 is analyzed by immunoprecipitation and immunoblotting. The obtained result is shown in FIG. 15. FIG. 15 is diagrams showing the result of immunoblotting analysis of products obtained by cisplatin treatment of SH-SY5Y cells. In the figure, "IP" means immunoprecipitation, and "IB" means immunoblotting.

The second diagram from the top in FIG. 15 is a diagram showing the result of immunoblotting analysis using anti-p53 antibody. From this diagram, the induction of endogenous p53 by cisplatin can be seen. The third diagram from the top in FIG. 15 is a diagram showing the result of immunoblotting analysis using anti-p21 antibody. From this diagram, it can be seen that p53 expressed during the cisplatin treatment promotes the expression of p21 downstream thereof, i.e., that it is an active form. The uppermost diagram in FIG. 15 is a diagram showing the result of immunoprecipitation of a cell lysate (homogenate) using anti-βAPP antibody, and immunoblotting analysis of the immunoprecipitate using anti-p53 antibody. From this diagram, it can be seen that p53 is present in the cisplatin treatment group, and that there is physical binding between a βAPP-derived product and p53. Since βAPP is present on the membrane and p53 is present in the nucleus, it is unlikely that there is physical binding therebetween. Therefore, this suggests that C60 or C58, which are cleavage products of βAPP, localizes to the nucleus and binds to p53. It is suggested that the induction of the death of SH-SY5Y cells by cisplatin is due to the activation of endogenous p53 accompanying the stabilization thereof, and that an interaction between a βAPP-derived product and p53 is functionally involved in that.

Nuclear localization of the βAPP-derived product C60:

A gene encoding C60 is artificially produced, and its expression and nuclear localization are examined. C60 is known to be very unstable, and therefore, the FLAG epitope is added to the C-terminal side.

Figure 16:
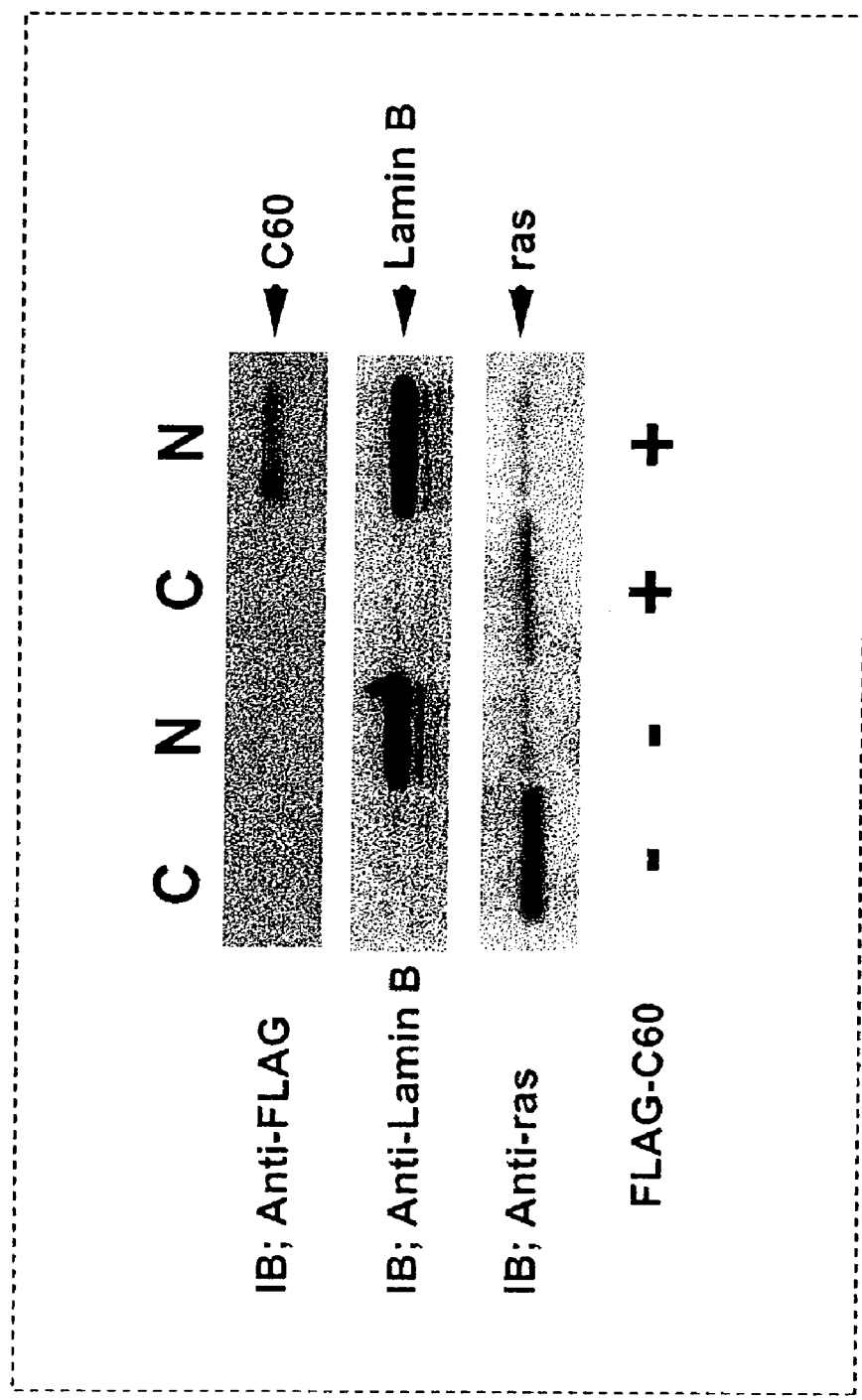
FIG. 16 is diagrams showing the result of immunoblotting analysis of the nuclear fraction and cytosolic fraction of U2OS cells in which C60 is forcibly expressed.

FLAG-labeled C60 is forcibly expressed in U2OS cells, the nuclear fraction and cytosolic fraction of the cells are prepared, and the distribution of C60 is analyzed by immunoblotting. The obtained result is shown in FIG. 16. FIG. 16 is a diagram showing the result of immunoblotting analysis of the nuclear fraction and cytosolic fraction of U2OS cells in which C60 is forcibly expressed. In the figure, "C" means the cytosolic fraction, and "N" means the nuclear fraction. "IB" means immunoblotting. LaminB, which is present in the nuclear matrix, is used as a nuclear marker. Ras, which is present in the cytoplasm, is used as a cytoplasmic marker. From FIG. 16, it can be seen that C60 is localized to the nucleus.

Figure 17:
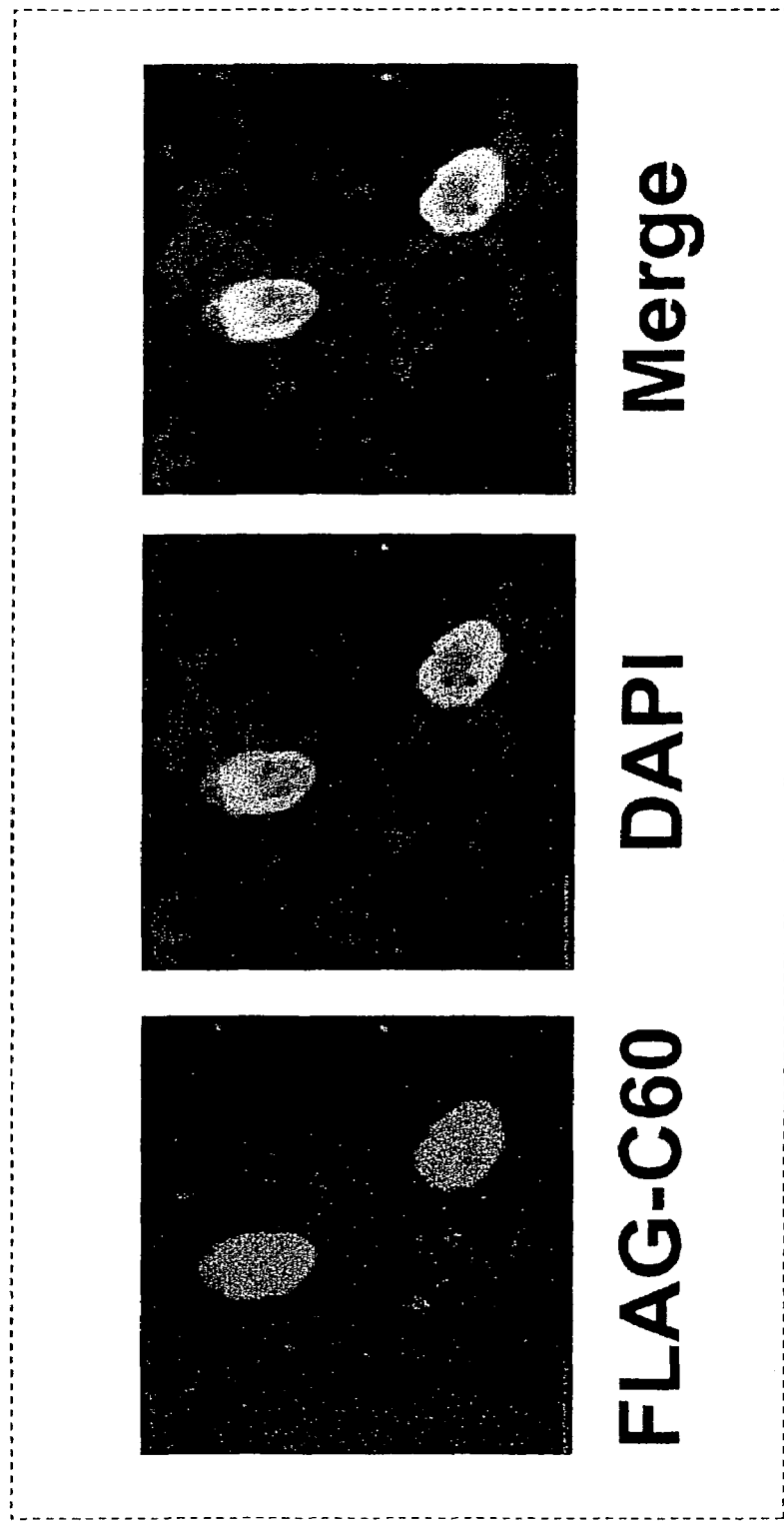
FIG. 17 is diagrams corresponding to confocal scanning micrographs of U2OS cells in which C60 is forcibly expressed and which are immunostained with anti-FLAG antibody.

Moreover, the distribution of C60 is biochemically observed by immunostaining using anti-FLAG antibody. The observation result obtained using a microscope is shown in FIG. 17. FIG. 17 is diagrams corresponding to confocal scanning micrographs of U2OS cells in which C60 is forcibly expressed and which are immunostained with anti-FLAG antibody. In the figure, "FLAG-C60" is a diagram corresponding to a micrograph showing the distribution of C60, "DAPI" is a diagram corresponding to a micrograph showing the distribution of the nuclear marker "DAPI", and "Merge" is a diagram corresponding to a composite photograph which is obtained by combining the two micrographs. From FIG. 17, it can be seen that the distribution of C60 and the distribution of DAPI overlap, showing the nuclear localization of C60.

Interaction of the βAPP-derived product C58 or C60 with p53:

The test results described above have already suggested that p53 interacts with βAPP, but it is further examined whether or not the interaction is its binding to C58 or C60.

Figure 18:
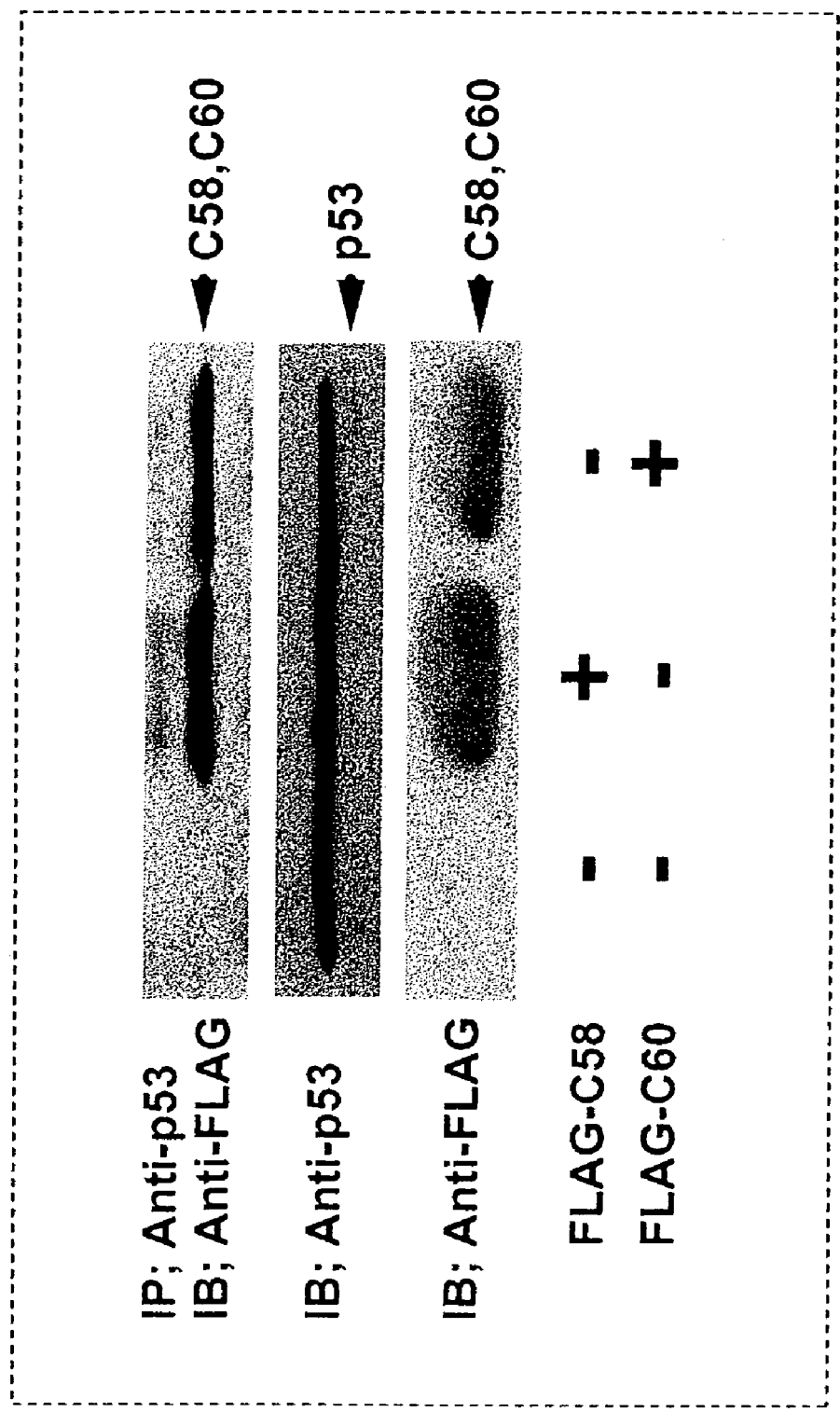
FIG. 18 is diagrams showing the result of immunoblotting analysis of COS7 cells in which C58 or C60 is forcibly expressed.

C58 or C60 labeled with FLAG is forcibly expressed in COS7 cells, and then the presence or absence of its interaction with p53 is studied by immunoprecipitation. The obtained result is shown in FIG. 18. FIG. 18 is diagrams showing the result of immunoblotting analysis of COS7 cells in which C58 or C60 is forcibly expressed. In the figure, "IP" means immunoprecipitation and "IB" means immunoblotting.

The uppermost diagram in FIG. 18 is a diagram showing the result of immunoprecipitation of a cell lysate (homogenate) using anti-p53 antibody, and immunoblotting analysis of the immunoprecipitate using anti-FLAG antibody. From FIG. 18, it can be seen that C58 and C60 are bound to p53. It is suggested that the activation of p53 by βAPP is a phenomenon mediated by physical binding of the βAPP-derived product C58 or C60 to p53.

Until now, it has generally been accepted that Alzheimer's disease occurs as a result of neuronal death caused by deposition of β42 or β40, which are cleavage products of βAPP, on cell membranes. However, from the test results described above, it can be seen that AICD, which is produced on the C-terminal side, localizes to the nucleus, interacts with p53 in the nucleus, enhancing the stability of p53, and that this increases the transcription factor activity, and unique activities of p53 such as cell proliferation-suppressing activity and cell death-inducing activity, and thereby induces neuronal death. In other words, it is suggested that the interaction between AICD and p53 is involved in the onset of Alzheimer's disease.

The above findings show that a drug which interferes with the interaction between AICD and p53 in the nucleus can be a drug for the prevention/treatment of Alzheimer's disease. If AICD does not localize to the nucleus, the interaction between AICD and p53 does not occur. Hence, the development of a drug which inhibits the nuclear localization of AICD is one possible approach. The development of a drug which decomposes AICD is another approach. The development of a drug which inhibits the interaction between AICD and p53 is still another approach. Incidentally, the development of drugs which suppress β- and γ-secretases, which are enzymes that produce AICD from βAPP, is already in progress (Tomita et al., cited above). The candidate drugs mentioned here are, for example, nucleic acids, proteins, other high molecular weight compounds, and low molecular weight compounds (chemically synthesized or natural).

(Agent for the Prevention and/or Treatment of Alzheimer's Disease)

The present invention provides an agent for the prevention and/or treatment of Alzheimer's disease containing c-Abl and/or $p_{19}^{ARF}$ as (an) active ingredient(s). It also provides an agent for the prevention and/or treatment of Alzheimer's disease containing AlcICD as an active ingredient. It further provides an agent for the prevention and/or treatment of Alzheimer's disease containing a peptide comprising the amino acid sequence set forth in SEQ ID NO: 1 or 2 of the Sequence Listing as an active ingredient. The peptide mentioned above may be synthesized by a method known in the art (for example, Merrifield's solid phase synthesis method).

These agents are obtained by mixing an effective amount of the active ingredient with a pharmaceutically acceptable carrier or with diluent and preparing a suitable dosage form from the mixture. Dosage forms suitable for administration are a tablet, a pill, a powder, a liquid, a suspension, an emulsion, a capsule, a suppository and an injection. They may be administered orally or non-orally to Alzheimer's disease patients, or to patients having a symptom of dementia as a prodrome for the disease.

(Method of Screening for a Drug for the Prevention and/or Treatment of Alzheimer's Disease)

The present invention provides a screening method wherein a candidate drug which inhibits the interaction between AICD and p53 in neurons is selected as a drug for the prevention and/or treatment of Alzheimer's disease. This screening method can be carried out using, for example, the two-hybrid system (e.g., Gyuris, J. Cell, 75, 791-803 (1993); Golemis, E. A., Current Protocols in Molecular Biology (John Wiley & Sons, Inc.) Ch. 20.0-20.1 (1996)).

This screening method is preferably carried out using an immunological technique. Specifically, this screening method preferably comprises:

a step of culturing neurons expressing AICD and p53 in which an AICD/p53 complex is formed, together with a candidate drug;

a step of obtaining a first immune complex which is a complex of AICD or p53 with a first antibody selected from an anti-AICD antibody and an anti-p53 antibody, and a second immune complex which is a complex of the AICD/p53 complex with the first antibody, by bringing a cell lysate prepared from the cultured neurons in contact with the first antibody;

a step of bringing the first and second immune complexes in contact with a second antibody which is selected from an anti-AICD antibody and an anti-p53 antibody, and which is different from the first antibody; and a step of detecting the presence of a third immune complex which is a complex of the second immune complex with the second antibody.

Specifically, an AICD molecule and a p53 molecule are expressed in neurons, and the cells are cultured together with a candidate drug for a given time, and then homogenized to obtain a cell lysate. The effect of the candidate drug on the interaction between the two molecules can be measured by immunoprecipitation with an antibody to one of the two molecules and detection/quantification of the other molecule contained in the precipitate using an immunological technique (immunoblotting or the like). Here, a drug for the prevention and/or treatment of Alzheimer's disease can be screened for by adding a suitable agonist and the candidate drug simultaneously to the culture system, performing the assay described above and comparing the immunoprecipitate with an immunoprecipitate prepared from cells which do not contain the candidate drug.

The present invention also provides a screening method wherein a candidate drug which inhibits the interaction between AICD and Fe65 in neurons is selected as a drug for the prevention and/or treatment of Alzheimer's disease. It further provides a screening method wherein a candidate drug which inhibits the interaction between AICD and Tip60 in neurons is selected as a drug for the prevention and/or treatment of Alzheimer's disease. Preferred embodiments of these screening methods are the same as that of the screening method described above, except that Fe65 or Tip60 is used instead of p53.

A drug for the prevention and/or treatment of Alzheimer's disease which can be obtained by any of the screening methods of the present invention may be administered orally or non-orally to Alzheimer's disease patients, or to patients having a symptom of dementia as a prodrome for the disease. The obtained drug is made into a pharmaceutical composition. Specifically, an effective amount of the drug is mixed with a pharmaceutically acceptable carrier or with diluent, and a suitable dosage form is prepared from the mixture. Dosage forms suitable for administration are a tablet, a pill, a powder, a liquid, a suspension, an emulsion, a capsule, a suppository and an injection.

EXAMPLES

Examples of the present invention will now be described, with the understanding that these examples are in no way limitative on the present invention.

(Cell Culture and Transfection)

COS7 cells and human osteosarcoma U2OS cells were maintained in Dulbecco's modified Eagle medium (DMEM) supplemented with 10% heat-inactivated fetal bovine serum (FBS, Life Technologies, Inc.), penicillin (100 IU/ml) and streptomycin (100 μg/ml). Human lung large cell carcinoma H1299 cells and human neuroblast SH-SY5Y cells were maintained in RPMI 1640 medium supplemented with 10% heat-inactivated FBS, penicillin (100 IU/ml) and streptomycin (100 µg/ml). The cells were cultured in air containing water-saturated 5% carbon dioxide gas at 37° C. Transient transfection was performed with each expression plasmid or a predetermined combination using FuGENE6 transfection reagent (Roche Molecular Biochemicals) according to the manufacturer's instructions. Transient transfection of U2OS cells or H1299 cells was performed using LipofectAMINE (Life Technologies, Inc.) according to the manufacturer's instructions.

(Luciferase Assay)

U2OS cells were proliferated in a 12-well plate ($5 \times 10^4$ cells/well), and the cells were transiently transfected using a given amount of expression plasmid for p53 and a p53-reactive luciferase reporter construct comprising the p21$^{WAF1}$, MDM2 or Bax promoter, and if required, a gradually increased amount of βAPP expression plasmid. The total amount of plasmid DNA per transfection was maintained at a constant amount (510 ng) using pcDNA3 (Invitrogen). 48 hours after the transfection, the transfected cells were collected, and washed with ice-cold 1×PBS. The luciferase activity was measured using Dual-Luciferase Reporter Assay System (Promega) according to the manufacturer's instructions.

(Colony Formation Assay)

U2OS cells were transfected in the presence or absence of a gradually increased amount of p53-encoding expression plasmid. 48 hours after the transfection, the cells were maintained in medium containing G418 (400 µg/ml (final concentration)). After 2 weeks of selection, the plate was stained with Giemsa. The drug-resistant colony count was determined.

(Cell Viability Assay)

The cell viability was determined by a modified 3-(4,5-dimethylthiazol-2-yl)-2,5-diphenyltetrazolium bromide (MTT) assay. Specifically, U2OS cells were plated on 100 µl of complete medium in a 96-well micro titer plate ($5 \times 10^3$ cells/well), and made to adhere thereto. On the next day, the medium was changed, and the cells were treated with cisplatin for 24 hours. In the MTT assay, 10 µl of MTT solution was added to each well, and incubated at 37° C. for 3 hours. The absorbance of the wells at 570 nm was measured using a microplate reader (Type 450, Bio-Rad Laboratories).

(Immunoprecipitation and Immunoblotting)

In the immunoprecipitation experiment, COS7 cells were transiently transfected with a suitable plasmid. 48 hours after the transfection, the cells were lysed in ice-cold phosphate buffered saline (PBS) and ice-cold EBC lysis buffer [50 mM Tris-HCl (pH 7.5), 120 mM NaCl, 0.5% (v/v) Nonidet P-40, and 1 mM phenylmethylsulfonyl fluoride (PMSF)], and the whole cell lysate was immunoprecipitated with anti-p53 monoclonal antibody (DO-1, Oncogene Research Products). The immunoprecipitate was analyzed by immunoblotting using anti-FLAG monoclonal antibody (M2, Sigma Chemical). The protein was visualized by enhanced chemiluminescence (ECL, Amersham Pharmacia Biotech) according to the manufacturer's instructions.

(Cell Fractionation)

Cells were divided into the cytosolic fraction and the nuclear fraction. First, transfected cells were washed twice with ice-cold 1×PBS, and the cells were lysed at 4° C. for 30 minutes in cell lysis buffer containing 10 mM Tris-HCl (pH 7.5), 1 mM EDTA, 0.5% NP-40 and protease inhibitor mix (Sigma Chemical). The cell lysate was centrifuged at 15000 rpm for 10 minutes, and the soluble fraction was collected as a cytoplasmic extract. The insoluble material washed with cell lysis buffer, and lysed in 1×SDS sample buffer, and the nuclear fraction was collected. The nuclear fraction and the cytosolic fraction were subjected to immunological analysis using anti-FLAG antibody, anti-LaminB monoclonal antibody (Ab-1, Oncogene Research Products) or anti-ras monoclonal antibody (RASK-3, Seikagaku Corpopration).

(Immunostaining)

U2OS cells were transiently transfected with an expression plasmid encoding FLAG-labeled C60. The cells which had been proliferated on a glass cover slip were fixed with 3.7% formaldehyde in 1×PBS at room temperature for 30 minutes, and the permeability was increased using 0.2% Triton X-100 at room temperature for 5 minutes. They were then blocked for 1 hour in 1×PBS containing 3% bovine serum albumin. The cells were washed with 1×PBS, and then incubated with anti-FLAG monoclonal antibody at room temperature for 1 hour. After the incubation with the primary antibody, the cells were washed, and incubated with secondary antibody-rhodamine conjugate (Invitrogen) at room temperature for 1 hour. The nucleus was stained with DAPI. The cells were finally washed with 1×PBS. The cover slip was removed from the plate, placed on a slide, and observed with a Fluoview laser scanning confocal microscope (Olympus).

INDUSTRIAL APPLICABILITY

As described above, according to the present invention, a drug/agent for the prevention and/or treatment of Alzheimer's disease having a mechanism of action which is different from that of, for example, an anti-amyloid antibody or β- or γ-secretase inhibitor can be developed, and new options for the prevention and/or treatment of Alzheimer's disease are therefore made available.

---

The invention claimed is:

1. A method for screening a compound for development of a drug, said method comprising:
   (a) culturing a neuron expressing APP intracellular C terminal domains (AICD) and p53 in a culture medium that is supplemented with cisplatin, wherein said neuron is cultured (i) in the presence of a compound and (ii) in the absence of the compound, respectively,
   (b) homogenizing the neuron obtained in step (a) to form a cell lysate,
   (c) contacting the cell lysate with a first antibody, to form an AICD/p53/first antibody immune complex, wherein said first antibody is selected from the group consisting of an anti-AICD antibody and an anti-p53 antibody,
   (d) detecting and quantifying the AICD/p53/first antibody immune complex from step (c),
   (e) comparing the amount of the AICD/p53/first antibody immune complex formed in the absence of the compound with the amount of the AICD/p53/first antibody immune complex formed in the presence of the compound, and
   (f) selecting the compound that decreases the amount of the AICD/p53/first antibody immune complex compared to the amount of the AICD/p53/first antibody immune complex formed in the absence of the compound, wherein said decrease in the amount of the AICD/p53 complex is indicative of the compound inhibiting binding between AICD and p53.

2. The method according to claim 1, wherein the step (d) is conducted by contacting the AICD/p53/first antibody immune complex with a second antibody, wherein the second antibody is selected from an anti-AICD or an anti-p53 antibody and is different from the first antibody.

3. The method according to claim 1, wherein said compound is selected from the group consisting of nucleic acid, protein, high molecular weight compound, and low molecular weight compound.

* * * * *

SEQUENCE LISTING

<160> NUMBER OF SEQ ID NOS: 2

<210> SEQ ID NO 1
<211> LENGTH: 136
<212> TYPE: PRT
<213> ORGANISM: Artificial
<220> FEATURE:
<223> OTHER INFORMATION: PTB2 domain

<400> SEQUENCE: 1

Gln Val Glu Phe Pro Ala Pro Lys Asn Glu Leu Val Gln Lys Phe Gln
 1               5                   10                  15

-continued

```
Val Tyr Tyr Leu Gly Asn Val Pro Val Ala Lys Pro Val Gly Val Asp
         20              25              30

Val Ile Asn Gly Ala Leu Glu Ser Val Leu Ser Ser Ser Ser Arg Glu
         35              40              45

Gln Trp Thr Pro Ser His Val Ser Val Ala Pro Ala Thr Leu Thr Ile
     50              55              60

Leu His Gln Gln Thr Glu Ala Val Leu Gly Glu Cys Arg Val Arg Phe
65              70              75                          80

Leu Ser Phe Leu Ala Val Gly Arg Asp Val His Thr Phe Ala Phe Ile
             85              90              95

Met Ala Ala Gly Pro Ala Ser Phe Cys Cys His Met Phe Trp Cys Glu
             100             105             110

Pro Asn Ala Ala Ser Leu Ser Glu Ala Val Gln Ala Ala Cys Met Leu
         115             120             125

Arg Tyr Gln Lys Cys Leu Asp Ala
     130             135

<210> SEQ ID NO 2
<211> LENGTH: 4
<212> TYPE: PRT
<213> ORGANISM: Artificial
<220> FEATURE:
<223> OTHER INFORMATION: NPTY sequence

<400> SEQUENCE: 2

Asn Pro Thr Tyr
1
```